United States Patent [19]

Kelner et al.

[11] Patent Number: 5,439,936

[45] Date of Patent: Aug. 8, 1995

[54] METHOD OF TREATING CERTAIN TUMORS USING ILLUDIN ANALOGS

[75] Inventors: Michael J. Kelner; Trevor C. McMorris, both of La Jolla, Calif.; Raymond Taetle, Tucson, Ariz.

[73] Assignee: The Regents of the University of California, Oakland, Calif.

[21] Appl. No.: 15,179

[22] Filed: Feb. 9, 1993

Related U.S. Application Data

[63] Continuation-in-part of Ser. No. 606,511, Oct. 31, 1990, which is a continuation-in-part of Ser. No. 416,395, Oct. 3, 1989, abandoned.

[51] Int. Cl.$^6$ .................... A61K 31/22; A61K 31/12
[52] U.S. Cl. .................... 514/546; 514/678; 514/681; 514/691
[58] Field of Search ............... 514/681, 546, 678, 691

[56] References Cited

PUBLICATIONS

Anchel et al., "The Biogenesis of Illudins S and M In Clitocybe Illudens*" *Phytochemistry* 9:2339–2343 (1970).

Anchel et al., "Antibiotic Substances From Basidiomycetes. VIII. Clitocybe Illudens*" *Proc. Natl. Acad. Sci. USA* 36(5):300–305 (1950).

Bransteterova et al., "HPLC determination of a new anticancer agent (acylfulvene) in serum*" *Neoplasma* 39(6):369–373 (1992).

Brandsteterova et al., "HPLC Analysis of Novel Anti–Cancer Agents–Illudins and Their Analogs" *J. Liquid chromatography* 16(1):115–125 (1993).

French et al., "Poisoning With The North American Jack O'Lantern Mushroom" *Clinical Toxicology* 26(1&2):81–88 (1988).

Hanson et al., "Studies in Terpenoid Biosynthesis. Part XV. Biosynthesis of the Sesquiterpenoid Illudin M" *J.C.S. Perkin I* 876–880 (1976).

Harttig et al., "Leaianafulvene, A Sesquiterpenoid Fulvene Derivative From Cultures of *Mycena Leaiana**" *Phytochemistry* 29(12):3942–3944 (1990).

Kelner et al., "Preclinical Evaluation of Illudins as Anticancer Agents" *Cancer Research* 47:3186–3189 (1987).

Kelner et al., "Preclinical Evalution of Illudins as Anticancer Agents: Basis for Selective Cytotoxicity" *J. Natl. Cancer Inst.* 82(19):1562–1565 (1990).

McMorris et al., "On the Mechanism of Toxicity of Illudins: The Role of Glutathione" *Chem. Res. Toxicol.* 3(6):574–579 (1990).

(List continued on next page.)

*Primary Examiner*—Jerome D. Goldberg
*Attorney, Agent, or Firm*—Schwegman, Lundberg & Woessner

[57] ABSTRACT

A therapeutic method is provided to inhibit tumor cell growth in a subject in need of said therapy is provided, comprising parenterally administering a therapeutic amount of a compound in a pharmaceutically acceptable carrier, wherein said compound has the structure:

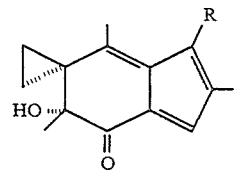

wherein R is selected from the group consisting of:

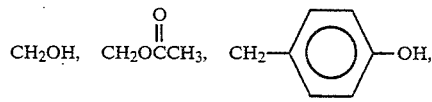

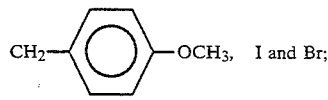

I and Br;

and wherein said tumor cell is sensitive to inhibition by said compound and is selected from the group consisting of a myeloid leukemia cell, a T-cell leukemia cell, a lung carcinoma cell, an ovarian carcinoma cell, and a breast carcinoma cell.

12 Claims, 9 Drawing Sheets

PUBLICATIONS

McMorris et al., "Fungal Metabolites. The Structures of the Novel Sesquiterpenoids Illudin-S and M" *J. Amer. Chemi. Society* 87(7):1594–1600 (1965).

McMorris et al., "Structure-Activity Relationships of Illudins: Analogs with Improved Therapeutic Index" *J. Org. Chem.* 57(25):6876–6883 (1992).

McMorris et al., "Structure and Reactivity of Illudins" *Tetrahedron* 45(17):5433–5440 (1989).

Shimomura, Osamu, "The Role of Superoxide Dismutase in Regulating the Light Emission of Luminescent Fungi" *J. of Experimental Botany* 43(256):1519–1525 (1992).

Tanaka et al., "Metabolism of illudin S, a toxic principle of *Lampteromyces japonicus*, by rat liver. I. Isolation and identification of cyclopropane ring-cleavage metabolites" *Xenobiotica* 20(7):671–681 (1990).

Tanaka et al., "Metabolism by rat liver cytosol of illudin S, a toxic substance of *Lampteromyces japonicus*. II. Characterization of illudin s-metabolizing enzyme" *Xenobiotica* 22(1):33–39 (1992).

Varki et al., "Cloned Low Metastatic Variants from Human Lung Carcinoma Metastases" *Anticancer Research* 10:637–644 (1990).

Walser et al., "Mode of Action of Illudin S" *Antimicrob. Ag. Chemother.* 3(3):357–362 (1973).

Weinreb, S. M., "Fulvenes Derived From Illudin S" *Tetrahedron Ltrs.* 38:3489–3491 (1971).

METHOD OF TREATING CERTAIN TUMORS USING ILLUDIN ANALOGS

This work was supported in part by research grant CA-37641 from the National Institutes of Health. The U.S. Government has rights in the invention.

This application is a continuation-in-part of U.S. Ser. No. 07/606,511, filed Oct. 31, 1990; which is a continuation-in-part of U.S. Ser. No. 07/416,395, filed Oct. 3, 1989, now abandoned the content of which is hereby incorporated by reference into the present application.

BACKGROUND OF THE INVENTION

Multiple agent chemotherapy has curative potential in some hematologic malignancies and advanced rapidly proliferating solid tumors. Curative chemotherapy has benefitted from the discovery of new, relatively non-cross resistant agents, and more effective use of existing agents. Interventions which increase the efficacy of conventional agents include more effective regimens for multiple drug administration, minimization of drug toxicities and increased use of adjuvant, surgical or radiation therapy.

Despite recent advances, patients with many types of malignancies remain at significant risk for relapse and mortality. After relapse, some patients can be reinduced into remission with their initial treatment regimen. However, higher doses of the initial chemotherapeutic agent or the use of additional agents are frequently required, indicating the development of at least partial drug resistance. Recent evidence indicates drug resistance can develop simultaneously to several agents, including ones to which the patient was not exposed. The development of multiple-drug resistant (mdr) tumors may be a function of tumor mass and constitutes a major cause of treatment failure. To overcome this drug resistance, high-dose chemotherapy with or without autologous bone marrow transplantation is employed. The high-dose chemotherapy may employ the original drug(s) or be altered to include additional agents. The feasibility of this approach has been demonstrated for hematopoietic and solid tumors. The development of new drugs non-cross resistant with mdr phenotypes is required to further the curative potential of current regimens and to facilitate curative interventions in previously treated patients.

Recently, the in vitro anti-tumor activity of a novel class of natural products called illudins was examined in Kelner, M. et al., *Cancer Res.* 47:3186 (1987), incorporated herein by reference. Illudin S and M are two types of illudins known to exist. Illudins have a chemical structure entirely different from other chemotherapeutic agents. Illudin compounds were previously purified and submitted for evaluation to the National Cancer Institute Division of Cancer Treatment (NCI DCT) in vivo drug screening program but had a low therapeutic index in other experimental tumor systems in accordance with NCI studies. The extreme toxicity of illudins has prevented any applications in human tumor therapy.

Thus, these exists a need for chemotherapeutic agents which are toxic to tumors, and especially mdr tumors, and have an adequate therapeutic index to be effective for in vivo treatment. The subject invention satisfies this need and provides related advantages.

SUMMARY OF THE INVENTION

A therapeutic method of inhibiting tumor cell growth in a subject in need of said therapy is provided, comprising parenterally administering a therapeutic amount of a compound in a pharmaceutically acceptable carrier, wherein said compound has the structure:

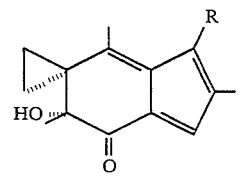

wherein R is selected from the group consisting of:

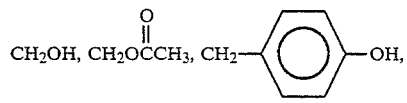

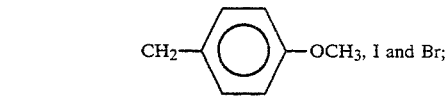

and wherein said tumor cell is sensitive, to inhibition by said compound and is selected from the group consisting of a myeloid leukemia cell, a T-cell leukemia cell, a lung carcinoma cell, an ovarian carcinoma cell, and a breast carcinoma cell.

DETAILED DESCRIPTION OF THE INVENTION

Figure 1:
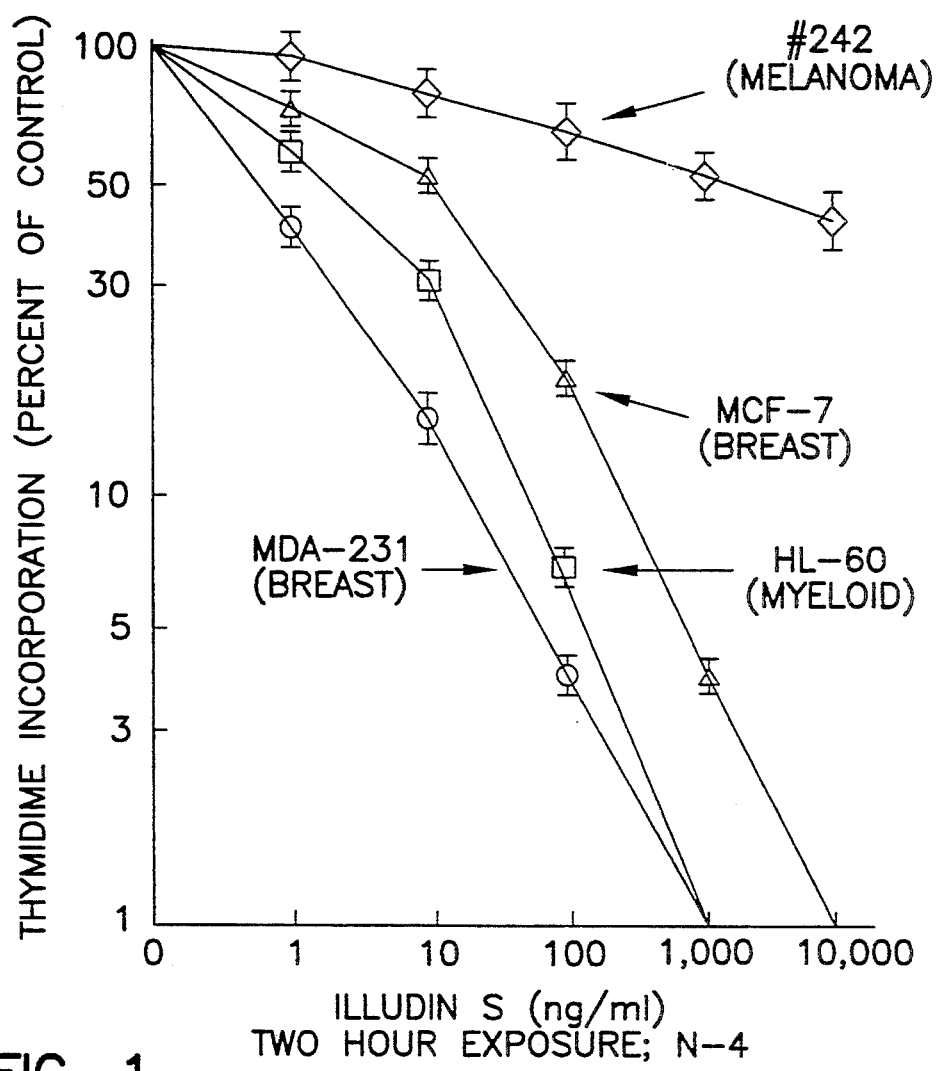
FIG. 1 shows the sensitivity of breast carcinoma and myeloid leukemia cells versus other tumors to illudin S.

A method of inhibiting tumor cell growth in a subject is provided comprising contacting the tumor with a therapeutic amount of an illudin S or illudin M analog having the structure:

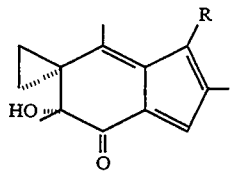

wherein R is

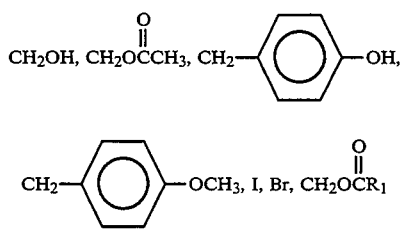

By "inhibiting" is meant either decreasing the tumor cell growth rate from the rate which would occur without treatment or causing the tumor cell mass to decrease in size. Inhibiting also includes a complete regression of the tumor. Thus, the analogs can either be cytostatic or cytotoxic to the tumor cells enumerated above.

The subject can be any animal having a myeloid leukemia, a T-cell leukemia, a lung carcinoma, an ovarian carcinoma or breast carcinoma. The analogs are effective on human tumors in vivo as well as on human tumor cell lines in vitro.

The tumors listed hereinabove can be contacted with the analog by any effective means, many of which are well known in the art. The route of administration to the subject can include intravenous, oral, intraperitoneal, and oral and nasal inhalation. The preferred route of administration depends on the subject and type of tumor encountered.

Applicants have made the surprising discovery that analogs of illudin S and M can be made which are less toxic than illudin S and M but are a more effective chemotherapeutic agent in vivo. As noted above, illudin S and M have a low therapeutic index due to the extreme toxicity and, therefore, cannot be used therapeutically in humans. Applicants have discovered that various modifications in illudin S and M inhibit nucleophiles from reacting with the compound. This results in less facile opening of the cyclopropane ring and reduces the toxicity of the compound in vivo while resulting in a high therapeutic index. The Applicants have made the further discovery that an acylfulvene analog, 6-hydroxymethylacylfulvene, is markedly more efficacious and nontoxic than previously known S and M illudin analogs.

The therapeutically effective amount of analog varies with the subject. However, it has been found that relatively high doses of the analogs can be administered due to the decreased toxicity compared to illudin S and M.

A therapeutic amount between 30 to 112,000 μg per kg of body weight has been found especially effective for intravenous administration while 300 to 112,000 μg per kg of body weight is effective if administered intraperitoneally. As one skilled in the art would recognize, the amount can vary depending on the method of administration. Further, the amount can vary if the analog is linked to a toxin. The methods of the invention are especially effective against tumor cells of myeloid, epidermoid, T-cell leukemia, and lung, ovarian and breast carcinoma.

EXAMPLE I

Synthesis of Dehydroilludin M

A mixture of illudin M (200 mg) and pyridinium dichromate (1 g) in dry dichloromethane (60 ml) was stirred at room temperature in a flask equipped with a rubber septum so that an atmosphere of argon could be maintained. After 20 hours, the reaction mixture was diluted with diethyl ether (20 ml) and filtered through a short column of silica gel. The column was further eluted with more diethyl ether and the combined filtrate was concentrated, giving a residue which was chromatographed on silica gel with hexane-ethyl acetate (10:1) as eluent. The desired compound was obtained in early fractions from the chromatography. The yield was 140 mg of white crystals melting at 64°–65° C. NMR spectral data were recorded for this compound.

EXAMPLE II

Synthesis of Fulvene

Illudin S (50 mg) was dissolved in water (2 mL) and 3N hydrochloric acid (2 mL) added to the solution. The resulting solution soon became cloudy (within 30 min) and a yellow precipitate formed. The mixture was placed in the refrigerator overnight; then it was extracted with chloroform (10 mL). The yellow chloroform solution was dried (MgSO4) and the solvent was removed under reduced pressure leaving an orange-yellow gum. This material was chromatographed on silica gel with hexanes: ethyl acetate (6:1) as eluent giving the fulvene (20 mg) and the bisfulvene (10 mg). NMR spectral data were recorded for these compounds.

Alternatively, a total synthesis of the fulvene can also be achieved in the following way:

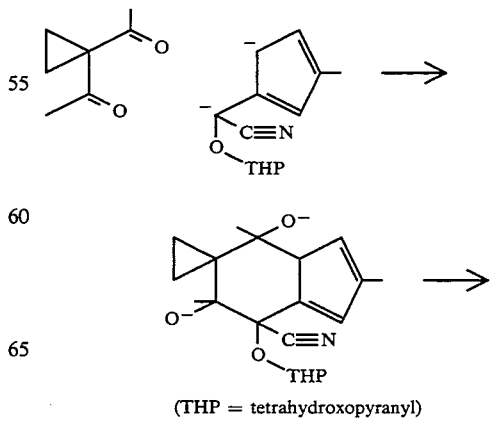

(THP = tetrahydroxopyranyl)

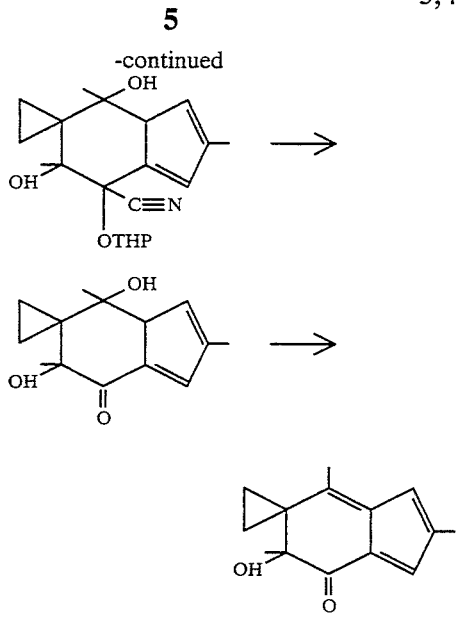

Reaction of the known 1, 1-diacetyl cyclopropane with the dianion of the cyclopentadiene derivative shown gives a diol which on mild acid treatment gives the diolketone. Selective elimination of a tertiary hydroxyl group gives the desired fulvene.

EXAMPLE III

In Vitro Studies

To assess cytotoxic effects, various concentrations of illudins were added to cultures of cells for 48 hours, then cell growth/viability was determined by trypan blue exclusion. As an alternative to 48 hour continuous exposure studies, cells were plated in liquid culture in 96 well plates, exposed to various concentrations of illudins for 2 hours, pulsed with [$^3$H]-thymidine for one to two hours and harvested onto glass filters. The filter papers were added to vials containing scintillation fluid and residual radioactivity determined in a beta (scintillation) counter.

When screening the sensitivity of other solid tumor cell lines to illudin S, a breast cell line, MCF-7, was noted to be markedly sensitive (FIG. 1). Another breast cell line maintained in our laboratory, MDA-231, was also found to be markedly sensitive to illudin S (FIG. 1).

Studies with dehydroilludin M indicated this analog also displayed selective toxicity towards myeloid leukemia cells and breast carcinoma lines MCF-7 and MDA-231 (Table 1).

TABLE 1

Histiospecific cytotoxicity of illudin S and dehydroilludin M as demonstrated by inhibition of thymidine after a two hour exposure to the toxins (N - 3).

| Compound | IC$_{50}$ (nM/L) | |
|---|---|---|
| | Illudin S | Dehydroilludin M |
| HL60, myeloid | 7 ± 1 | 246 ± 19 |
| 8392, B-cell | 236 ± 31 | >38,000 |
| 8402, T-cell | 669 ± 196 | >38,000 |
| 242, melanoma | 607 ± 70 | >38,000 |
| 547, ovarian | 607 ± 110 | >38,000 |
| SL-2, murine (thymic) | 142 ± 15 | 5,235 ± 277 |
| MCF-7, breast | 58 ± 5 | 653 ± 65 |
| MDA-231, breast | 2.0 ± 0.2 | 112 ± 17 |

Because previous studies showed that CEM mdr variants were not resistant to illudin S, several other mdr cell types were studied for susceptibility to illudin S and the dehydroilludin M. These mdr daughter cell lines demonstrate a 200 to 800 fold increase in resistance to multiple conventional chemotherapeutic agents, but showed minimal or no resistance to illudin S or dehydroilludin M (Table 2). Thus, mdr cells associated with or without the gp170 protein were still susceptible to illudin toxicity. These studies indicate that illudins' novel structure confers relative non-cross resistance in multidrug resistant hematopoietic cell lines. The derivative of illudins, dehydroilludin M, is slightly less toxic than the parent illudin compound, but results (Table 2) indicate that there is no cross-resistance to this compound in various mdr cell lines.

The effect of illudin S and dehydroilludin M on L1210, murine bone marrow CFU-gm, and C1498 (AML cell line) was studied. Illudin S was the most potent agent ever tested in this assay and displayed the largest differential effect ever noted between L1210 and AML leukemia lines and CFU-gm zone cites (Table 3). The derivative, dehydroilludin M, while less toxic was markedly more selective towards the AML line. It inhibited AML colony formation at concentrations where it had no effect on the CFU-gm cells (Table 4).

TABLE 2

Sensitivity of Different Mdr Lines to Illudin S

| MDR cell line available | | Illudin S | Dehydroilludin M |
|---|---|---|---|
| CEM Variants | Parent | 8.3 ± 2.6 | nt |
| | VM-1 | 16.2 ± 6.4 | nt |
| | AraC | 14 | nt |
| | VLB100 (gp170+) | 3.7 ± 0.7 | nt |
| | Dox (gp170+) | 14 | |
| MDA-231 (Breast) | Parent | 0.85 ± 0.23 | 54 ± 7 |
| | 3-1 (gp170+) | 0.89 ± 0.38 | 58 ± 11 |
| MCF7-wt (Breast) | Parent | 0.88 ± 0.11 | 92 ± 15 |
| | ADR (GSH-transferase) | 3.7 ± 0.4 | 68 ± 15 |
| HL-60 | Parent | 3.1 ± 1.1 | 163 ± 11 |
| | ADR (gp150+) | 1.9 ± 0.8 | 191 ± 44 |
| KB variant | Parent | 0.58 ± 0.12 | 125 ± 14 |
| | C-1 (gp170+) | 0.69 ± 0.15 | 80 ± 18 |
| | VBL (gp170+) | 0.69 ± 0.11 | 78 ± 19 |
| L1210 | Parent | 0.42 ± 0.08 | 62 ± 8 |
| | DDPt (cis-plat) | 0.46 ± 0.12 | 119 ± 39 |
| | BCNU | 0.58 ± 0.08 | 100 ± 31 |
| | PAM (melphalan) | 0.62 ± 0.15 | 73 ± 31 |
| | CPA (cyclophos) | 0.46 ± 0.12 | 38 ± 15 |

TABLE 3

Inhibition of Growth by Illudin S

| Illudin S Concentration (ug/disc) | Zone of Inhibition | | |
|---|---|---|---|
| | L1210 | Go | Colon 38 |
| 2.50 | 500 | 240 | 30 |
| 1.25 | 400 | 70 | 0 |
| 0.63 | 320 | 30 | 0 |

TABLE 4

Effect of Illudins on Colony Formation

| Compound | Dilution | Zone Size | | |
|---|---|---|---|---|
| | | L1210 | CFU-GM | C1498 (AML) |
| Illudin S | 1/1,000 | 850 | 400 | >1000 |
| | 1/4,000 | 600 | 200 | 800 |
| | 1/16,000 | 550 | 0 | 550 |
| | 1/64,000 | 300 | 0 | 250 |
| Dehydroilludin M | 1/25 | 400 | 200 | >1000 |
| | 1/125 | 200 | 100 | 750 |
| | 1/125 (repeat) | 300 | 50 | 700 |

TABLE 4-continued

| | | Effect of Illudins on Colony Formation | | |
|---|---|---|---|---|
| | | | Zone Size | |
| Compound | Dilution | L1210 | CFU-GM | C1498 (AML) |
| | 1/625 | 100 | 0 | 400 |

EXAMPLE IV

Structure Function Studies

Figure 2:
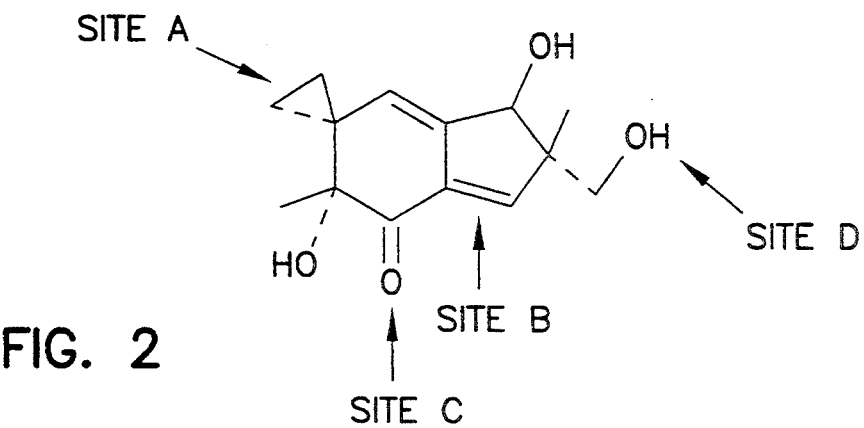
FIG. 2 shows the active sites of illudin S.

The structure-function studies were performed by synthesizing derivatives of the illudins and examining their in vitro toxicity for HL60 leukemia cells (Table 5). This study identified three critical sites for illudin toxicity. These include the cyclopropane ring (site A), the alpha/beta unsaturated bond site (site B), and the ketone group (site C) (FIG. 2). Alteration of any of these sites resulted in up to a 4 log decrease in toxicity. In contrast, the non-ring primary hydroxyl group (FIG. 2, site D) does not contribute to toxicity. Various large chemical groups can be attached to this site without altering toxicity. Many of the derivatives with a marked decrease in toxicity (as compared to illudin S or M) are still more potent than conventional chemotherapeutic agents such as BCNU or cis-platinum (Table 5).

TABLE 5

| IC$_{50}$ for Various Illudin Derivatives Versus Other Agents in HL-60 cells | |
|---|---|
| COMPOUNDS | nM |
| Illudin S or M | 10 |
| Dihydroilludin S or M | 100,000 |
| Acylfulvene | 500 |
| Dehydroilludin M (diketone) | 246 |
| Isoilludin M | 3,800 |
| Ptaquiloside | 7,700 |
| Pterosin C | 12,500 |
| 2,5,6,7-tetramethylindenone | 475 |
| Illudin tosylate | 38 |
| DNA polymerase inhibitor: Aphidocolin | 2,100 |
| Alkylating agent: BCNU | 23,300 |
| Crosslinking agent: cis-platinum | 550 ± 14 |
| Alkylating agent: MNNG | 15,000 |
| Protein Synthesis Inhibitor: Ricin | 0.2 |

EXAMPLE V

Structure-Function Studies: Chemical

Figure 3:
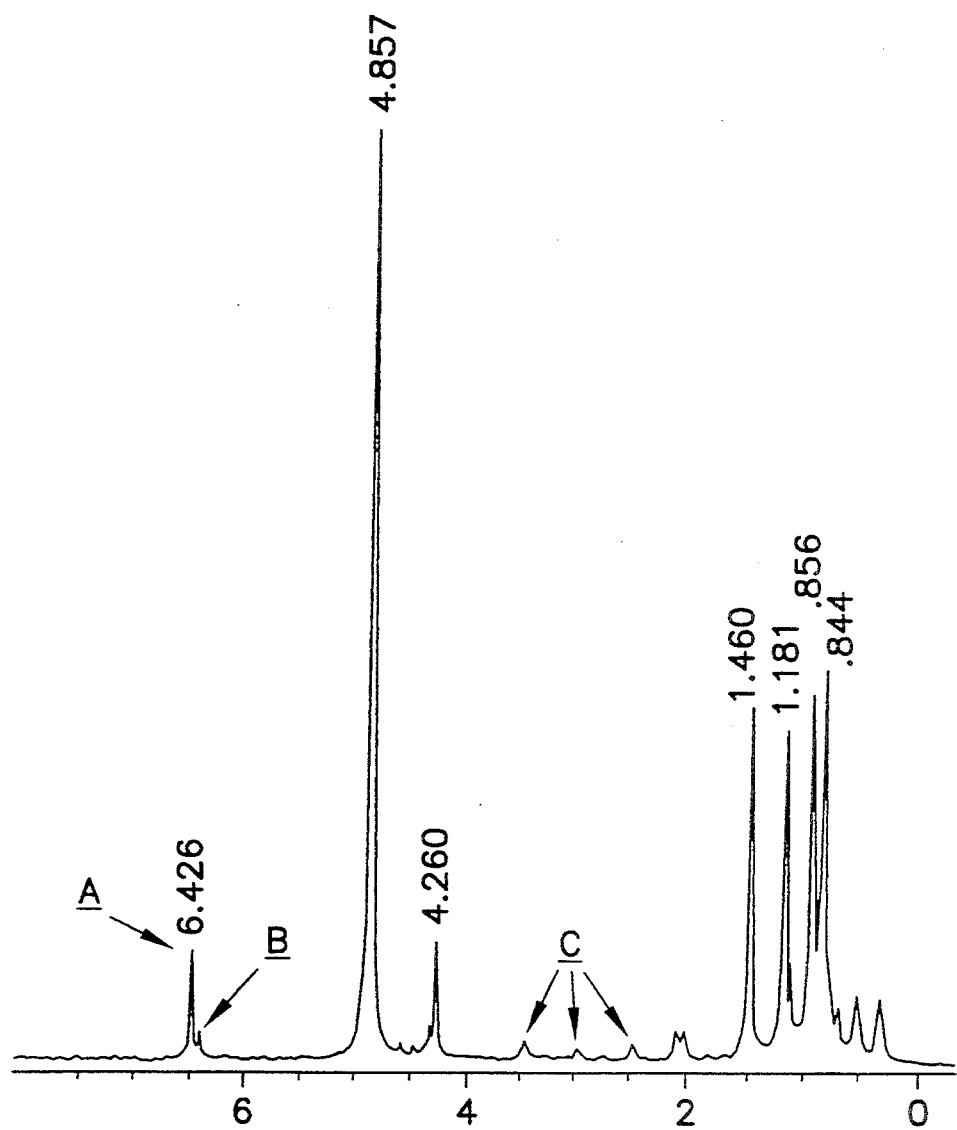
FIG. 3 shows an NMR spectrum demonstrating the presence of a short acting intermediate in acid. Signal A is from the hydrogen on the double bond in the 5 membered ring (illudin M). Signal B is from the hydrogen atom on the short lived intermediate that results from the cyclopropane ring opening up (but before the double bond reacts). Signals marked at C are from the product that results when the double bond has reacted. With time, the signal peaks from illudin M will disappear and the peaks at position C will be the predominate signals. Signal B will disappear concurrently with Signal A confirming it is a short lived intermediate arising from illudin M.

Illudin M is readily converted to stable aromatic compounds (on treatment with dilute HCl) which in cell culture studies are more than 1,000 fold less toxic. The chlorine-carbon bond formation, cyclopropane ring opening and extrusion of the tertiary hydroxyl (as water) are synchronous. The intermediate formed can be detected by NMR spectroscopy of the reaction mixture (FIG. 3). The intermediate, however, is highly reactive and is quickly converted to a phenol by attack of a second nucleophile, i.e., water. Thus, under acidic conditions, illudin M is clearly bifunctional.

The above studies indicate that the toxicity of illudins is related to the ease with which the tertiary hydroxyl can be removed and the cyclopropane ring opened. It was found that illudin toxicity depends on the combined effects of the cyclopropane group (site A, FIG. 2), the two double bonds (conjugated diene) (site B), and the ketone (site C). It was hypothesized that oxidation of the secondary hydroxyl group in the five membered ring to a ketone would alter the potency or selectivity of the molecule by contributing to further electron delocalization within the molecule. The new ketone group acts as an "electron sink" so that electrons of the cyclopropane C-C bonds are delocalized towards the ketone rather than to the carbon atom bearing the tertiary hydroxyl. This means the incipient carbocation, forming as the carbon-oxygen (oxygen of the tertiary hydroxyl) bond breaks, is not as stable as in the case of illudin M. Therefore, carbon-oxygen bond breaking is less favorable and reactivity is reduced. This ketone derivative, termed dehydroilludin M, was synthesized and was less toxic to HL-60 cells in vitro than illudin S or M (Table 4). As discussed above, the toxicity of dehydroilludin M appeared relatively selective for myeloid and breast carcinoma cells in vitro (FIG. 1 and Table 1).

Consistent with the above hypothesis are the results of the kinetics of the reaction of illudin M and dehydroilludin M with dilute HCl. In dilute HCl, illudin M undergoes a pseudo first-order reaction (k=4.7×10$^{-3}$ min$^{-1}$, tl/2=148 minutes) Dehydroilludin M also demonstrated first-order kinetics but the reaction was considerably slower (k=2×10$^{-4}$ min$^1$ tl/2=2765 min). In the reaction with dehydroilludin M, no intermediate could be detected by NMR spectroscopy. Presumably it formed too slowly and is too short-lived to be detected. The lower reactivity shown by dehydroilludin M suggests it is more selective in its reaction with nucleophiles and thus has a lower toxicity compared to illudin M.

The reaction of illudins with a naturally occurring nucleophile, glutathione has also been studied. At a wide pH range, from pH 3 to pH 9, glutathione spontaneously reacts with illudin M, illudin S, or dehydoilludin M, producing products analogous to those from the reaction of illudin M and HCl. The reaction rate is optimized at a pH of 6.1 to 7.0, indicating the reaction could occur intracellularly.

The toxicity of illudins towards a breast cell carcinoma line MCF7-wt and its MDR resistant daughter line MCF/Adr was then studied. The gp170 negative daughter cell line is drug resistant on the basis of a 50 fold increase in glutathione transferase, which results in a 200 to 800 fold decrease in sensitivity to conventional chemotherapeutic agents. This line also shows a 4.1 fold decrease in glutathione content. This daughter line showed a 4.2 fold decrease in sensitivity to illudin S (parent IC$_{50}$ 0.88 nmoles/1; daughter line 3.70 nanomoles/1) versus the 200 to 800 fold seen with other agents. Kinetic studies on the ability of illudins to inhibit glutathione transferase indicated there was no direct inhibition of enzyme activity. These findings show that while illudin toxicity is inversely correlated with intracellular glutathione content it is not correlated with glutathione transferase activity.

EXAMPLE VI

Animal Studies

Figure 4:
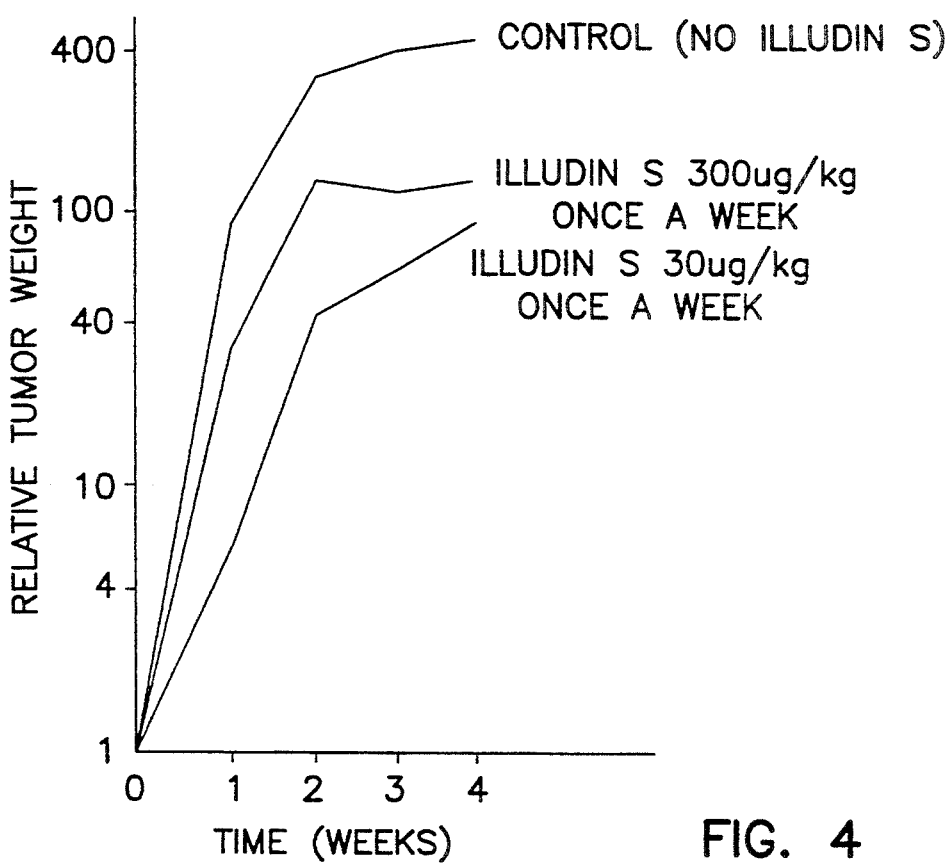
FIG. 4 shows the effect of illudin S on Molt-4 tumor growth in athymic mice (Balb/c).

Using procedures set forth in Leonard, J. E. et al., Cancer Res. 47:2899-02 (1987) and Dillman, R. O. et al, Cancer Res. 45:5632-36 (1985), both incorporated by reference herein, Molt-4 (human T-cell leukemia) xenografts were established in four week old athymic Balb/c nu/nu mice. After 3 weekly doses of total body radiation (600 cGy), mice were given subcutaneous flank injections of Molt-4 cells together with irradiated (6000 cGy) HT-1080 feeder cells. Two animals received only irradiated HT-1080 feeder cells to ensure these cells did not induce tumors. Animals were monitored for Molt-4 tumor development and when tumors were palpable (approximately 4×4 mm at 5 to 7 days), mice were randomized into groups of 5 as previously described. Control mice received intraperitoneal saline and treated mice received either 300 μg/kg illudin S, 30 or 300 μg/kg dehydroilludin M, IP twice weekly. In mice given illudin S there was tumor growth delay (FIG. 4).

Figure 5:
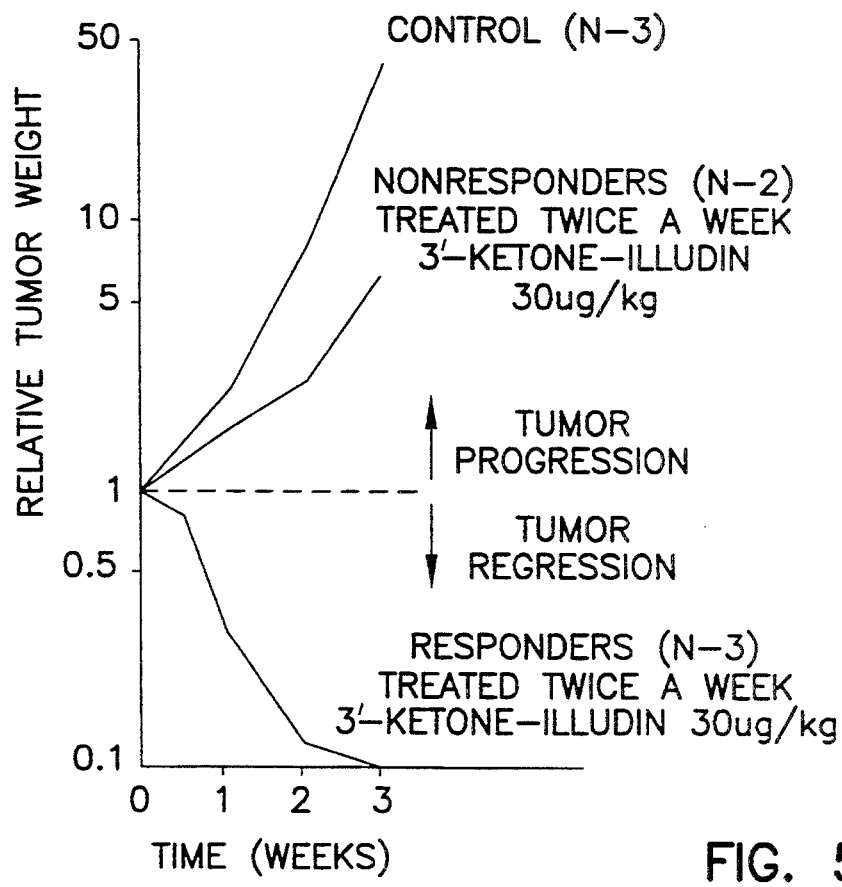
FIG. 5 shows the effect of dehydroilludin M on tumor growth.

In contrast, in nude mice which received the dehydroilludin M at the low dosage of 30 μg/kg (the compound was subsequently found to be nontoxic to mice at 60,000 μg/kg IP twice a week), three of five tumors underwent complete regression, but two tumors failed to respond (FIG. 5). The two apparently resistant tumors were harvested and tested in vitro for resistance to illudin S and dehydroilludin M. There was no evidence of resistance to either compound. Two of the complete responders were followed for over twelve weeks without evidence of tumor regression.

Using a different source of athymic nude mice, these experiments were repeated. In these studies there was little effect of illudins on tumor growth. The reason for this variability in response to Molt-4 xenografts probably relates to the low doses of dehydroilludin M, interanimal variations in glutathione metabolism, or drug distribution.

The efficacy of dehydroilludin M was then screened in a syngeneic model using murine SL-2 cells. SL-2 leukemia/lymphoma cells are injected subcutaneously and metastasized to lymph nodes, spleen, and lungs, and drug efficacy in this model is determined by increased life span (ILS). The SL-2 cells were administered at 2.5 million cells per animal and treatment was delayed for 7 days until the tumors were palpable. This is a relatively stringent test against established tumors and contrasts to general drug screens in the SL-2 model which normally use only 0.5 million cells and starting drug treatment at 3 days. Dehydroilludin M had a little effect at 30 mg/kg IP twice a week, ILS 5%, and 60 mg/kg IP twice a week, ILS 18%. When administered IV at 0.03 mg/kg, twice a week, the ILS increased to 38%. This suggests the drug is metabolized by the liver and is likely more efficacious when administered IV.

During the course of these in vivo experiments, it became clear from in vitro experiments, that histiospecificity of illudins depends upon the presence of an active energy-dependent pump. The SL-2 and the Molt-4 cells were studied and it was determined that the uptake mechanism was not present. Therefore, the studies were redirected into xenograft models that used cells of myeloid lineage.

Figure 6:
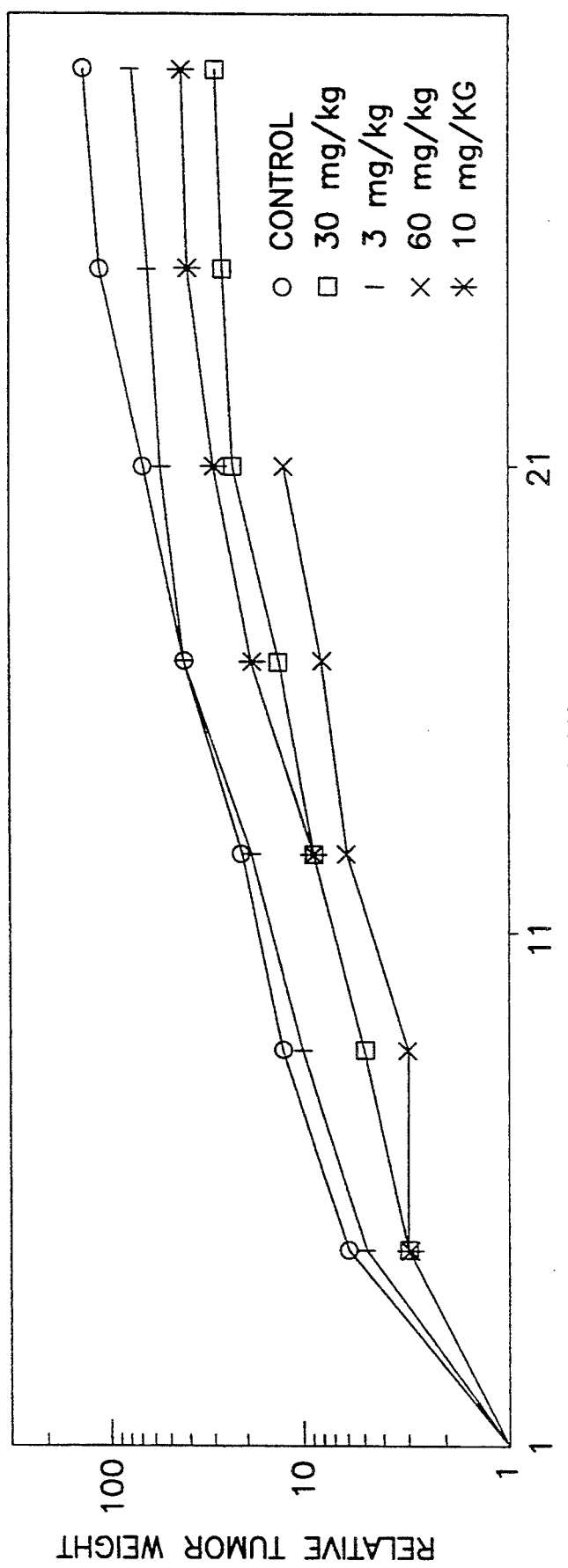
FIG. 6 shows the response of HL60/MRI xenograft to dehydroilludin M.

Human HL-60 cells capable of growing as xenografts in nude mice without animal radiation were obtained from Dr. Theodore Brightman (NCI). These cells termed HL-60 MRI cells, were confirmed to have energy-dependent uptake pump, a not unexpected finding as their parental cells possess the pump. Dehydroilludin M induced dose related tumor inhibition when administered IP on a twice a week schedule (FIG. 6). The MTD IP dose for dehydroilludin M was reached in these studies on the 2 dosages per week IP dose schedule. Similar tumor regressions have been observed with IV dehydroilludin M.

In collaboration, the in vivo effects of dehydroilludin M was again studied. Initially the compound was studied against L1210 cells. A dose of 2.5 mg/kg IP given daily for 5 days resulted in an ILS of only 9%. The dehydroilludin M was then administered as a 24 hour infusion (5.0 mg/kg); the ILS was 11%. After we became aware of the presence of the energy-dependent uptake in human myelocytic cells, dehydroilludin M was screened for in vivo efficacy against a syngeneic mouse AML model using C1498 cells and a single bolus of illudin S, 2.5 mg/kg IP, produced an ILS of 35%. A second trial using the same dosage, administered IP once a day for 5 days resulted in a 44% ILS. As the animals can tolerate 60 mg/kg IP or 1 mg/kg IV (tail vein) on a twice a week schedule for 4 weeks without demonstrating weight loss or a decrease in food/water intake, it is possible to further optimize both dosage and treatment schedule.

EXAMPLE VII

HL60/MRI Mouse Experiment With Acylfulvene and Dehydroilludin M

Thirty mice were injected subcutaneously, over the shoulder, with 500,000 HL60/MRI cells (human myeloid leukemia tumor cells). Treatment was begun on day 11, rather than immediately. This delay in starting treatment is a stringent test; to determine whether a compound is effective. By delaying treatment, the tumor cells become firmly established.

The mice were divided into 6 groups of 5 each. One group was the control and these animals received on a placebo, the solution used to dilute the agent. The other groups received the following compounds and dosages: the dehydroilludin M compound at 1.0 mg/kg, the dehydroilludin M at 3.0 mg/kg, the Acylfulvene at 0.3 mg/kg, the Acylfulvene at 1.0 mg/kg, the Acylfulvene at 3.0 mg/kg. All animals received the placebo or drugs by intravenous injection using a tail vein. The placebo or drugs were administered on a twice a week schedule.

Results are summarized in the accompanying table 6. Both the dehydroilludin M and the Acylfulvene compound were effective at inhibiting tumor growth and demonstrated dosage dependence inhibition (the more drug administered, the less the tumors grew). The animals receiving the highest amount of either drug did not display any evidence of adverse effect, such as a decrease in food or water intake, nor a statistically significant decrease in body weight. These results show that higher dosages of either drug can be administered. Also, that the drug could be administered on a more effective dosage schedule, such as on a daily basis.

TABLE 6

Summary: HL60/MRI experiment, intravenous - #1
BY TOTAL TUMOR WEIGHT [Mg]

|  | DAY 11 | DAY 18 | DAY 25 | DAY 32 | DAY 40 |
|---|---|---|---|---|---|
| CONTROL | | | | | |
| No Drug | 99 ± 36 | 845 ± 282 | 3299 ± 1080 | 10162 ± 4123 | 16747 ± 5061 |
| Dehydroilludin M | | | | | |
| 1 mg/kg IV | 114 ± 55 | 883 ± 311 | 2274 ± 992 | 6025 ± 1772 | 11507 ± 3707 |
| 3 mg/kg IV | 101 ± 40 | 911 ± 309 | 2127 ± 1092 | 2854 ± 1260 | 4784 ± 2303 |

TABLE 6-continued

| | Summary: HL60/MRI experiment, intravenous - #1 BY TOTAL TUMOR WEIGHT [Mg] | | | | |
|---|---|---|---|---|---|
| | DAY 11 | DAY 18 | DAY 25 | DAY 32 | DAY 40 |
| Acylfulvene | | | | | |
| 0.3 mg/kg IV | 73 ± 38 | 540 ± 167 | 1352 ± 520 | 3204 ± 1147 | 9501 ± 4605 |
| 1 mg/kg | 58 ± 32 | 582 ± 297 | 964 ± 685 | 2321 ± 1434 | 6275 ± 2865 |
| 3 mg/kg | 38 ± 30 | 369 ± 250 | 336 ± 215 | 437 ± 238 | 1201 ± 501 |

EXAMPLE VIII

General In Vitro Screening Procedures and Cell Uptake Studies

In keeping with the suggestions of the previous examples and our concentration on mechanisms of illudin action and tissue specificity, other myeloid leukemia cell lines can be screened for rapid illudin uptake (KG1, KG1a, HEL, K562, OCI-Ml, AML-193).

The procedures for in vitro screening of illudin compounds are detailed in the previous examples. Cytotoxicity of new analogs for cell lines is initially evaluated over a 5 log range using growth or semi-solid colony forming assays, and inhibition of thymidine incorporation. Inhibition of thymidine incorporation is used because earlier studies indicate that thymidine incorporation is preferentially inhibited by illudins and correlates closely with cell death. Analogs are screened against normal bone marrow progenitors and a variety of cell lines involving various leukemias, B and T cell) and solid tumors (melanoima, ovarian).

In vitro testing of dehydroilludin M on various cell lines, including MDR lines, can also be performed on DNA-repair deficient cell lines and normal bone marrow progenitors. A variety of other analogs can be prepared. Since these analogs will have alterations in the known active sites, they are expected to result in a similar tumor inhibition. Screening studies for these analogs can include various mdr cells (to ensure that no cross-resistance occurs) and DNA-repair deficient cell lines.

In vitro testing can also study sensitivity of other breast cell lines to determine if they are also preferentially sensitive to illudin S, dehydroilludin M, and the fulvene analog.

EXAMPLE IX

Assessment of Illudin Uptake in Tumor Cells

While human myeloid tumor cells are sensitive to illudins, their normal precursors, granulocyte/macrophage forming units, are relatively resistant to illudins by 1.5 to 2.0 logs, demonstrating that the transport system is absent from some normal marrow cells and providing a therapeutic margin of safety.

Figure 7:
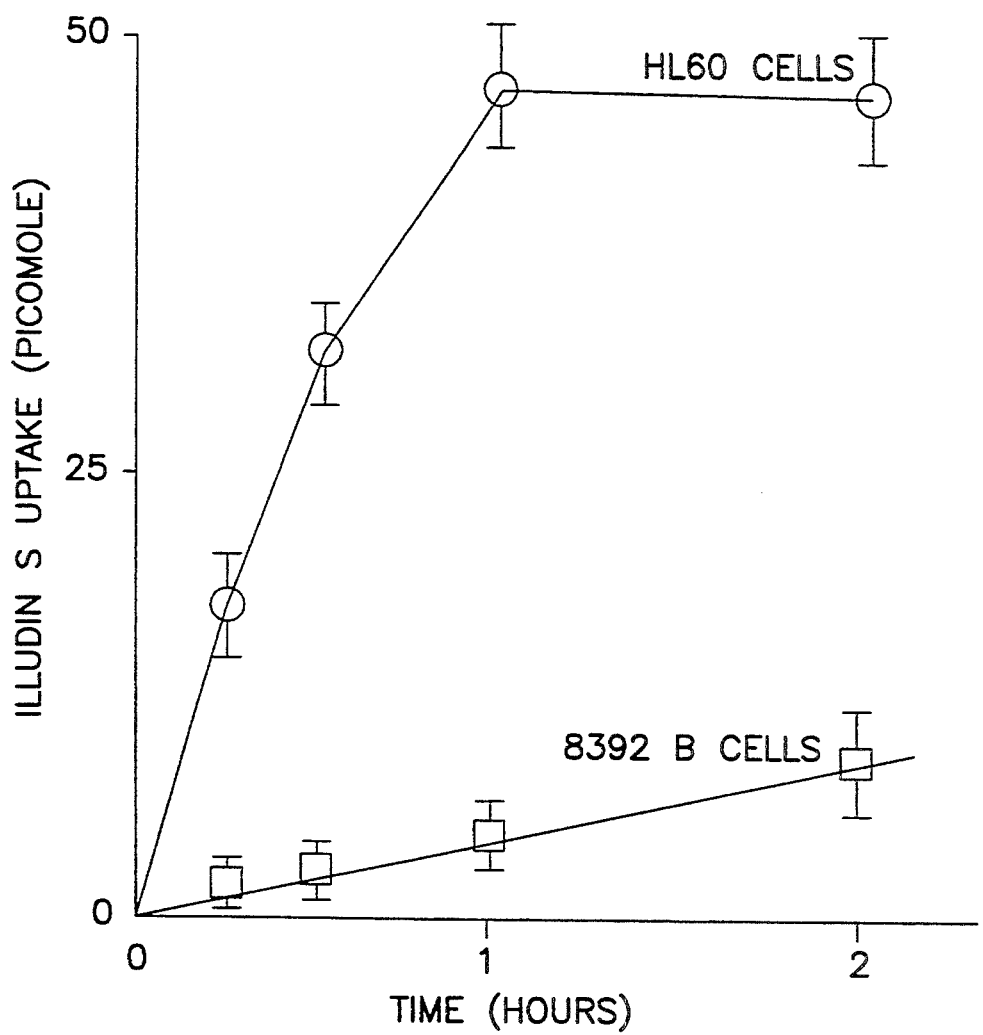
FIG. 7 shows illudin S uptake using relatively sensitive HL60 cells and resistant B cells.
Figure 8:
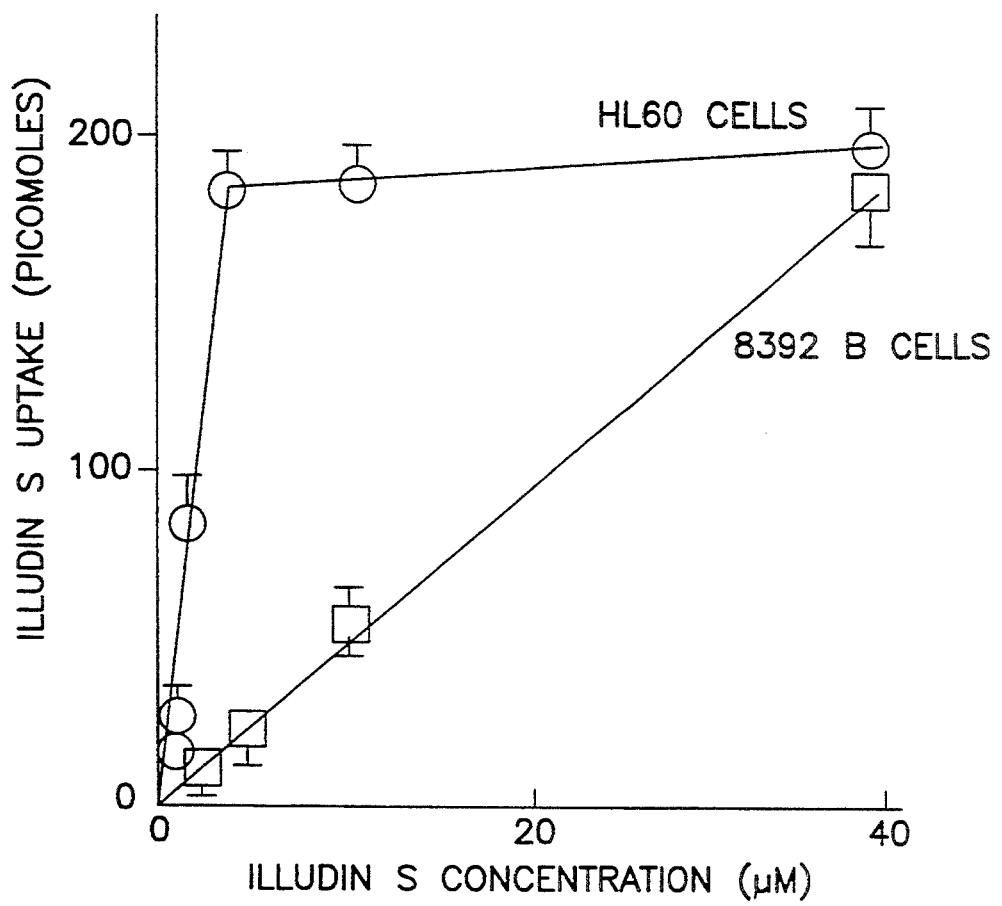
FIG. 8 shows the rapid intracellular accumulation of illudin S by HL60 cells was saturated at high concentrations.
Figure 9:
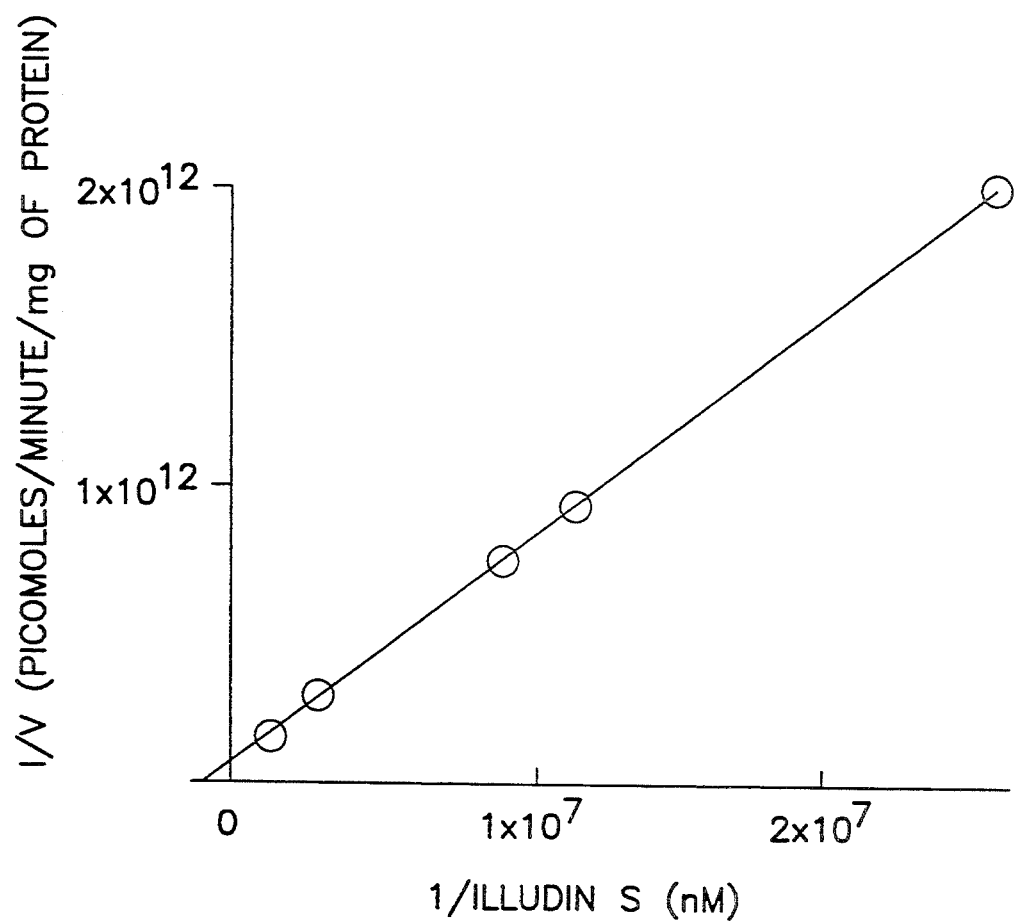
FIG. 9 shows the analysis of the initial uptake of illudin S by HL60 cells at varying concentrations conformed to Michaelis-Menton saturation constants.

Specific illudin S uptake was assayed using relatively sensitive HL60 cells and resistant B cells. At 37° C., HL60 myeloid leukemia cells demonstrated rapid uptake of illudin S, while the relatively insensitive 8392 B-cells exhibited comparatively little drug incorporation (FIG. 7). The intracellular accumulation of illudins in the B cell line was slow and linear for 7 hours (r−0.984), at which time the intracellular concentration approached that of the incubation mixture. HL60 cells, in contrast, rapidly accumulated the toxin and intracellular accumulation reach a plateau within one hour. HL60 cells exposed to 10 nM illudin S concentrated the toxin 19 fold, whereas B cells did not actively concentrate the toxin. The rapid intracellular accumulation of illudin S by HL60 cells was saturated at high concentrations (FIG. 8). In contrast, illudin S accumulation in 8392 B cells remained concentration dependent. Analysis of the initial uptake of illudin S by HL60 cells at varying concentrations revealed that the influx of illudin S conformed to Michaelis-Menton saturation kinetics (FIG. 9). The Vmax for HL60 cells was 27 picomoles/minute/mg of protein and the Km was 4.2 $\mu$M. This indicates HL60 cells have a very high transport capacity for illudins as the Vmax for illudins is 5 times the Vmax for folate, a vitamin required by cells.

Cold (4° C.), 1% azide, and the metabolic blockers 2-deoxyglucose and antimycin A, all block uptake of illudin S into HL60 cells but have little effect on the insensitive 92 B-cells (Table 7). These studies indicate that illudin S is transported and concentrated into HL60 cells by an energy dependent transport system, whereas the transport into insensitive B-cells occurs only by diffusion (passive or nonenergy requiring transport). MCF7 breast tumor cells also demonstrated inhibition of uptake by cold. The finding of an energy-dependent transport mechanism explains why myeloid and breast tumor cells are so sensitive to illudins with short exposure times, but B-cells are not.

TABLE 7

| Uptake of [³H] Illudin S by HL60 Myeloid versus 8392 B-cells | | | |
|---|---|---|---|
| Maximum uptake per hour (picomoles)[a] | | | |
| Conditions | HL60 | 8392 | MCF7 |
| 37° C. | 75 ± 16[b] | 5.5 ± 1.4 | 29 ± 4 |
| 4° C. | 4.3 ± 0.9 | 3.4 ± 1.0 | 4.0 ± 2.1 |
| 1% Azide | 8.7 ± 1.4 | 4.3 ± 1.3 | NT[b] |
| 2-deoxyglucose & Antimycin A | 16.7 ± 3.5 | 3.6 ± 1.4 | NT |

[a]per 10 million cells
[b]NT = not tested

Cells were exposed to 100 ng/ml of [³H]-labeled illudin S for one hour and harvested as described. Results are expressed as mean ±SE and represent 3 experiments.

EXAMPLE X

Synthesis and Structure of 2,5,6,7-Tetramethyl-1-Indenone and Dehydropterosin Compounds First 2,4,5,6-tetramethyl-1,3-indanione was synthesized by preparing a solution of 1,2,3-trimethylbenzene and methylmalonylchloride in carbon disulfide and adding aluminum trichloride dropwise over two hours. The mixture was relfuxed for 2 more hours, crushed ice added, and extracted three times with chloroform. The combined extract was washed with brine, dried, and solvent removed to leave a residue which was purified by chromatography with 1% ethyl acetate in benzene.

Removal of solvent and purification by sublimation gave the desired product.

The 2,5,6,7-tetramethyl-1-indenone was prepared by reducing 2,4,5,6-tetramethyl-1,3-indanione with zinc dust at 50° C. Product was purified by chromatography with 1% ethyl acetate in benzene to yield two isomers. The major isomer was treated with 10% potassium hydroxide, then purified by sublimation. The compound has the structure:

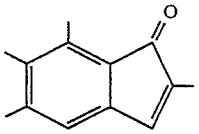

Dehydropterosin O synthesis: 3-acetoxy-6(beta-methoxy) ethyl-2,5,7-trimethyl-1-indanone was dissolved in tetrahydrofuran and 10% potassium hydroxide and refluxed for two hours. The solution was then extracted three times with ether and the combined extracts chromatographed with 2% ethylacetate in benzene to yield the Dehydropterosin O compound. The compound has the structure:

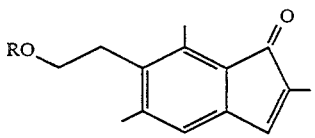

R=H Dehydropterosin B
R=CH₃ Dehydropterosin O

Both compounds were toxic to cells in vitro and have antifungal properties.

EXAMPLE XI

Synthesis of Acylfulvene Analogs

Many acylfulvene analogs possessing the key structural features required for antitumor activity may be prepared starting from illudin S or by total synthesis from simple precursors. Illudin S is produced by fermentation of *Omphalotus illudens*. On dissolving this compound in water and adding dilute $H_2SO_4$ it is converted to the acylfulvene ($R_1$=H, $R_2$=H, $R_3$=CH₃) in 55% yield. A large number of analogs may be obtained from the acylfulvene by modifying the $R_2$ substituent, e.g., $R_2$=hydroxymethyl, bromo, iodo, chloro, fluoro, nitro, p-hydroxybenzyl, p-methoxybenzyl. $R_2$ can also be polynuclear or heterocyclic aromatic groups.

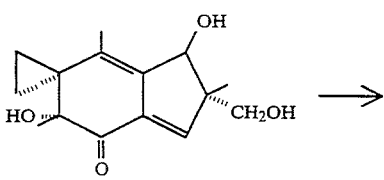

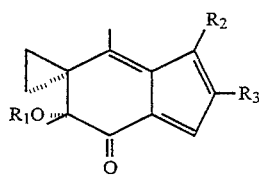

The $R_1$ group may be acyl or alkyl. Analogs with different $R_3$ groups (and also $R_2$ groups) can be prepared by total synthesis as outlined.

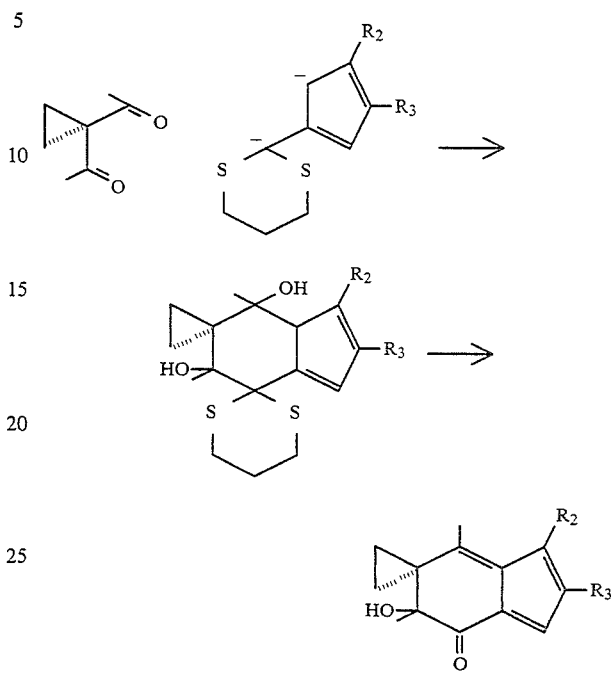

Aldol condensation of 1,1-diacetylcyclopropane with the dianion derived from an appropriately substituted cyclopentadiene gives an intermediate which is readily converted to the acylfulvene. A wide variety of compounds are possible since $R_2$ and $R_3$ may be alkyl, aryl or substituted alkyl or aryl groups.

Synthesis of acylfulvene. Illudin S 2 g (9.2 mmol) was dissolved in 700 mL water followed by addition of 4 M $H_2SO_4$ (236 mL). The solution was stirred overnight, and extracted with ethyl acetate. The organic phase was washed with saturated $NaHCO_3$, water and brine, dried over $MgSO_4$ and concentrated. Chromatography on silica with hexane and ethyl acetate afforded 0.82 g acylfulvene (50%). ¹H NMR δ0.73 to 1.50 (m, 4 H), 1.38 (s, 3 H), 2.00 (s, 3 H), 2.15 (s, 3 H), 3.93 (s, 1H), 6.43 (s, 1 H), 7.16 (s, 1 H); MS m/Z 216 (M+), 202 (M+-CH₂), 188 (M+-CH₂CH₂), 173 (M+-2CH₂CH₃), 170 (M+-2CH₂-H₂O). UV 325 nm (8.3×10³), 235 nm (16.6×10³). The compound has the structure:

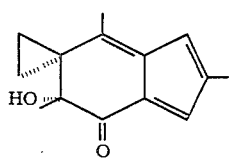

Synthesis of 6-hydroxymethylfulvene. Acylfulvene (550 mg, 2.5 mmol) was dissolved in 40 mL THF and 30% formaldehyde-water solution (40 mL) was added. 4 N $H_2SO_4$ solution (26.4 ml) was added to bring the final concentration of $H_2SO_4$ to 1 N The solution was stirred overnight and extracted with ethyl acetate. The organic phase was washed with saturated $NaHCO_3$ solution, water and brine and dried over $MgSO_4$. Chromatography on silica gel with hexane and ethyl acetate gave 400 mg hydroxymethylfulvene (64%). ¹H NMR δ0.72 to 1.48 (m, 4 H), 1.38 (s, 3 H), 2.15 (s, 3 H), 2.19 (s, 3 H), 3.90 (s, 1 H), 4.66 (d, J=2.1 Hz, 2 H), 7.10 (s, 1 H). MS m/Z 246 (M+), 228 (M+-H$_2$O), 218 (M+-CH$_2$CH$_2$), 186 (M+-CH$_3$-CH$_2$-CH$_2$-OH), 185 (M+-H$_2$O-CH$_2$-CH$_2$-CH$_3$). UV 233 nm (1.0×10$^4$), 325 nm (7.7×10$^3$). The compound has the structure:

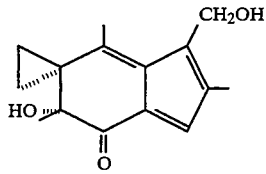

Iodofulvene. To a solution of acylfulvene (60 mg, 0.28 mmol) in 15 ml CH$_2$Cl$_2$ was added silver trifloroacetate (63 mg, 0.29 mmol). A solution of iodine (70.5 mg, 0.28 mmol) in 8 mL CH$_2$Cl$_2$ was added dropwise at 0° C. The mixture was stirred at that temperature for 3 hours then filtered through celite and eluted with ether. Concentration of the filtrate gave iodofulvene as a red gum (73 mg, 77%). $^1$H NMR δ0.76 to 1.54 (m, 4 H), 1.38 (s, 3 H), 2.14 (s, 3 H), 2.36 (s, 3 H), 3.87 (s, 1 H), 7.16 (s, 1 H). MS m/Z 342 (M+), 314 (M+-CH$_2$CH$_2$), 299 (M+-CH$_2$CH$_2$-CH$_3$), 29 6 (M+-CH$_2$CH$_2$-H$_2$O), 215 (M+-I), 187 (M+-I-CH$_2$CH$_2$), 127 (I+). The compound has the structure:

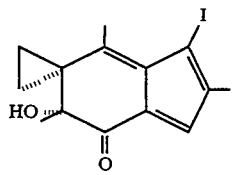

Bromofulvene. Acylfulvene (60 mg, 0.28 mmol) was dissolved in 9 ml acetonitrile at 0° C. N-bromosuccinimide (50 mg, 0.28 mmol) was added and the mixture was stirred at that temperature for 3.5 hours. Water was used to quench the reaction and ether to extract the product. The ether layer was washed with water and brine and dried over MgSO$_4$. Chromatography gave bromofulvene as orange crystals (77 mg, 94%; recrystalized from ether acetate-hexane, m.p.. 92°-94° C.). $^1$H NMR δ0.75 to 1.55 (m, 4 H), 1.40 (s, 3 H), 2.12 (s, 3 H), 2.33 (s, 3 H), 3.89 (s, 1 H), 7.15 (s, 1 H). MS m/Z 295 (M+), 293 (M+-2), 267, 265, (M+-CH$_2$CH$_2$), 252, 250 (M+-CH$_2$CH$_2$-CH$_3$), 249, 247 (M+-CH$_2$CH$_2$-H$_2$O), 2 15 (fulvene-1). The compound has the structure:

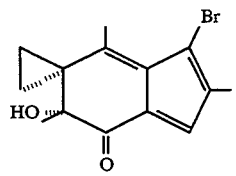

p-Hydroxybenzylfulvene. Phenol (40 mg, 0.4 mmol) was added to a solution of hydroxymethyl-fulvene (70 mg, 0.28 mmol) in dry CH$_2$Cl$_2$ (25 mL). The mixture was cooled to −78° C. and boron triflouride etherate (0.3 mL, 2.7 mmol) was added dropwise.. The reaction was stirred at that temperature for 1 hour and water was added to quench the reaction. The organic layer was washed with H$_2$O, NaHCO$_3$ and brine, and dried over MgSO$_4$. Chromatography on silica gel with hexane-ethyl acetate yielded 90 mg (98%) of red crystals (m.p. 143°-144° C). $^1$H NMR δ0.59-1.43 (m, 4 H), 1.36 (s, 3 H), 1.76 (s, 3 H), 2.07 (s, 3 H), 3.95 (s, 1 H), 3.97 (d, J=7.2 Hz, 2 H), 4.83 (s, 1 H), 6.74 (d, J=8.4 Hz, 2 H), 6.91 (d, J=8.4 Hz, 2 H), 7.22 (s, 1 H). MS m/Z 322 (M+), 294 (M+-2 CH$_2$), 279 (M+-2 CH$_2$-CH$_3$), 251 (M+-2 CH$_2$-CH$_3$CO), 215, 107 UV 228 nm (12×10$^4$, with inflections at 243 and 262 nm), 325 (7.1×10$^3$), 410 nm (2.6×10$^3$). The compound has the structure:

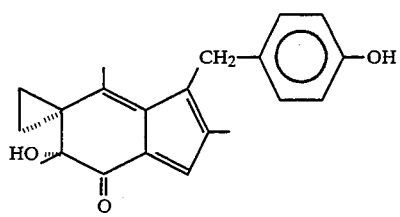

p-Methoxybenzylfulvene. Anisole (0.04 mL, 0.37 mmol) was added to a solution of hydroxymethylfulvene (10 mg, 0.04 mmol) in dry CH$_2$Cl$_2$ (5 mL). The mixture was cooled to −78° C. and boron triflouride etherate (0.04 mL, 0.36 mmol) was added dropwise. The reaction was stirred at that temperature for 1 hour and water was added to quench the reaction. The organic layer was washed with H$_2$O, saturated NaHCO$_3$ and brine, and dried over MgSO$_4$. Concentration of the solution gave a residue which was dried in vacuo, yielding the product in quantitative yield (14 mg). $^1$H NMR δ0.59-1.40 (m, 4 H). 1.36 (s, 3 H), 1.76 (s, 3 H), 2.07 (s, 3 H), 3.78 (s, 3 H), 3.95 (s, 1 H), 3.99 (d, J=16.12 Hz, 2 H), 6.81 (d, J-8.8 Hz, 2 H), 6.96 (d, J=8.3 Hz, 2 H), 7.22 (s, 1 H). MS m/Z 336 (M+), 308 (M+-CH$_2$CH$_2$), 215, 121 ((CH$_2$-Ph-OCH$_3$)+). UV 410 nm (2.7×10$^3$), 325 nm (7.0×10$^3$), 267 nm (1.0×10$^4$), 245 nm (inflection), 226 nm (1.9×10$^4$), 203 nm (1.4×10$^4$). The compound has the structure:

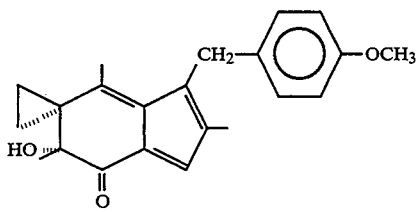

EXAMPLE XII

In Vitro Cell Culture Studies of Acylfulvene Analogs

In vitro testing using cell culture assays demonstrated the 6-hydroxymethylacylfulvene, bromoacylfulvene, and iodoacylfulvene analogs were markedly toxic to the target tumor cells HL60 and MV522 at both 2 and 48 hour exposure periods (Table 8 and Table 9). The relative toxicity ratio (2 to 48 hour toxicity) suggested these analogs would be more efficacious in vivo than either the parent Illudin S compound or the analogs described in the original patent application.

TABLE 8

2 hour cytotoxicity of new analogs (as determined by inhibition of thymidine incorporation compared to original analogs and Illudin S

| | 2 hour IC50 values (nanomoles/liter) | | |
|---|---|---|---|
| | HL60 Cells | 8392 Cells | MV522 |
| Illudin S | 10 ± 1 | 236 ± 22 | 19 ± 6 |
| Dehydroilludin M | 377 ± 81 | 61,335 ± 9,810 | 1,826 ± 378 |
| Acylfulvene | 998 ± 244 | 66,435 ± 13,006 | 727 ± 180 |
| 6-hydroxymethyl-acylfulvene | 150 ± 11 | 7,359 ± 2,096 | 114 ± 28 |
| acetate analog of 6-HMAF | 3,333 ± 192 | 47,455 ± 2,951 | 1,066 ± 87 |
| bromo-acylfulvene | 803 ± 88 | 17,175 ± 890 | 4,180 ± 424 |
| iodoacylfulvene | 2,602 ± 345 | 10,331 ± 497 | 956 ± 152 |
| p-hydroxybenzylfulvene | 264 ± 38 | 95,236 ± 11,984 | 1,180 ± 180 |
| p-methoxybenzylfulvene | 1,964 ± 84 | 35,714 ± 7,292 | 2,045 ± 208 |

TABLE 9

48 hour cytotoxicity of new analogs compared to original analogs and the parent Illudin S compound.

| | 48 hour IC50 values (nanomoles/liter) | | |
|---|---|---|---|
| | HL60 Cells | 8392 Cells | MV522 |
| Illudin S | 3 ± 1 | 8 ± 2 | 4 ± 1 |
| Dehydroilludin M | 296 ± 66 | 269 ± 100 | 313 ± 23 |
| Acylfulvene | 364 ± 74 | 833 ± 152 | 349 ± 23 |
| 6-hydroxymethyl-acylfulvene | 4 ± 1 | 76 ± 4 | 73 ± 8 |
| acetate analog of 6-HMAF | 806 ± 30 | 4,434 ± 163 | 486 ± 42 |
| bromoacylfulvene | 412 ± 21 | 1,186 ± 138 | 356 ± 61 |
| iodoacylfulvene | 290 ± 12 | 1,696 ± 183 | 556 ± 47 |
| p-hydroxybenzylfulvene | 382 ± 39 | 11,078 ± 388 | 615 ± 56 |
| p-methoxybenzylfulvene | 1,051 ± 104 | 7,143 ± 244 | 1,548 ± 214 |

EXAMPLE XIII

In Vivo Studies

Figure 10:
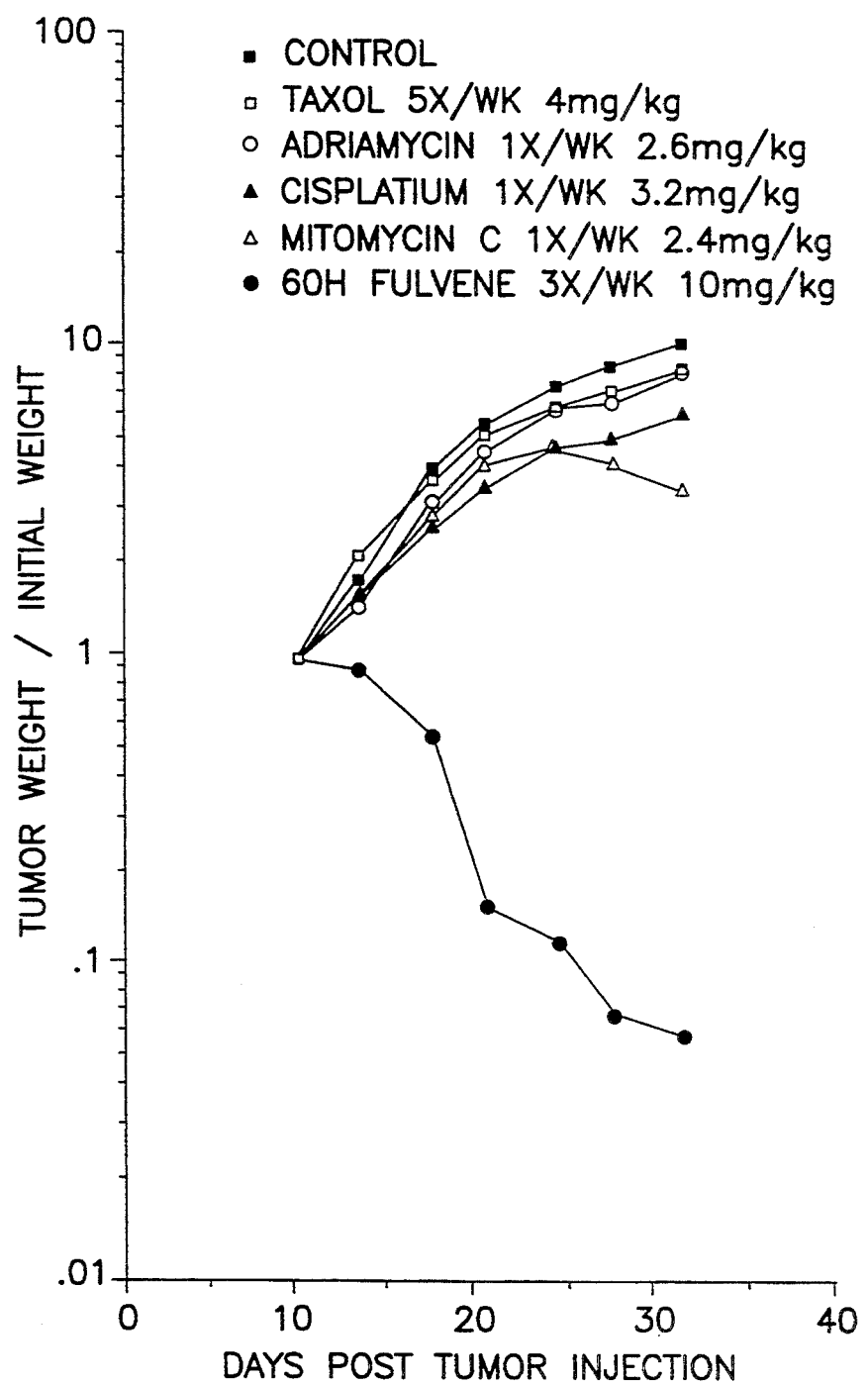
FIG. 10 shows the effect of 6-hydroxymethylacylfulvene and other conventional anticancer agents on human lung adenocarcinoma MV522.

Based on these in vitro screening results, one of the analogs, the 6-hydroxymethylacylfulvene, was chosen for in vivo studies to determine if the analog was indeed more potent than the acylfulvene. The xenograft was again the human lung adenocarcinoma MV522 as it is a nonresponsive model to conventional anti-cancer agents and kills by metastasis (not local tumor invasion). The conventional anti-cancer agents cis-platinum, taxol, mitomycin C, adriamycin, as well as Illudin S were chosen as pharmaceutical controls. A control group was included that received only the solvent used to dissolve the drugs, a 40% dimethylsulfoxide/normal saline mixture (40% DMSO/NS). The 6-hydroxymethylacylfulvene analog actually induced tumor regression in animals. Actual regression of tumors by an anti-cancer agent has never been noted before in this model. There was no inhibition of tumor growth by conventional anticancer agents or by Illudin S (FIG. 10). Animals received only 9 doses of the 6-hydroxymethylacylfulvene analog. There was no evidence of toxic side effects in these animals as evidenced by a decrease in activity, weight gain, food intake, or water intake. There was no significant increase in the life span of cisplatinum, taxol, mitomycin C, and Adriamycin treated animals as compared control (DMSO/NS) treated animals. The Illudin S actually caused premature death (drug toxicity) (Table 10). The 6-hydroxymethylacylfulvene treated animals lived significantly longer than controls (DMSO/NS treated), cisplatinum, taxol, mitomycin C, and Adriamycin treated animals ($p < 0.001$ for all groups) (Table 10).

TABLE 10

Efficacy of 6-hydroxymethylacylfulvene analog, versus other agents, in the human lung adenocarcinoma MV522 metastatic lung tumor model - First experiment

| | drug | life span |
|---|---|---|
| controls DMSO/NS | IP 3×/WK | 100 ± 7% |
| cis-platinum | 3.2 mg/kg IP 1×/WK | 102 ± 8% |
| taxol | 4.0 mg/kg IP 5×/WK | 100 ± 10% |
| mitomycin C | 2.4 mg/kg IP 1×/WK | 111 ± 2% |
| Adriamycin | 2.6 mg/kg IP 1×/WK | 98 ± 12% |
| Illudin S | 2.5 mg/kg IP 3×/WK | <26% |
| | | [5/5 dead at only 3 doses] |
| 6-hydroxymethylacylfulvene | 10 mg/kg IP 3×/WK | 233 ± 18% |

Figure 11:
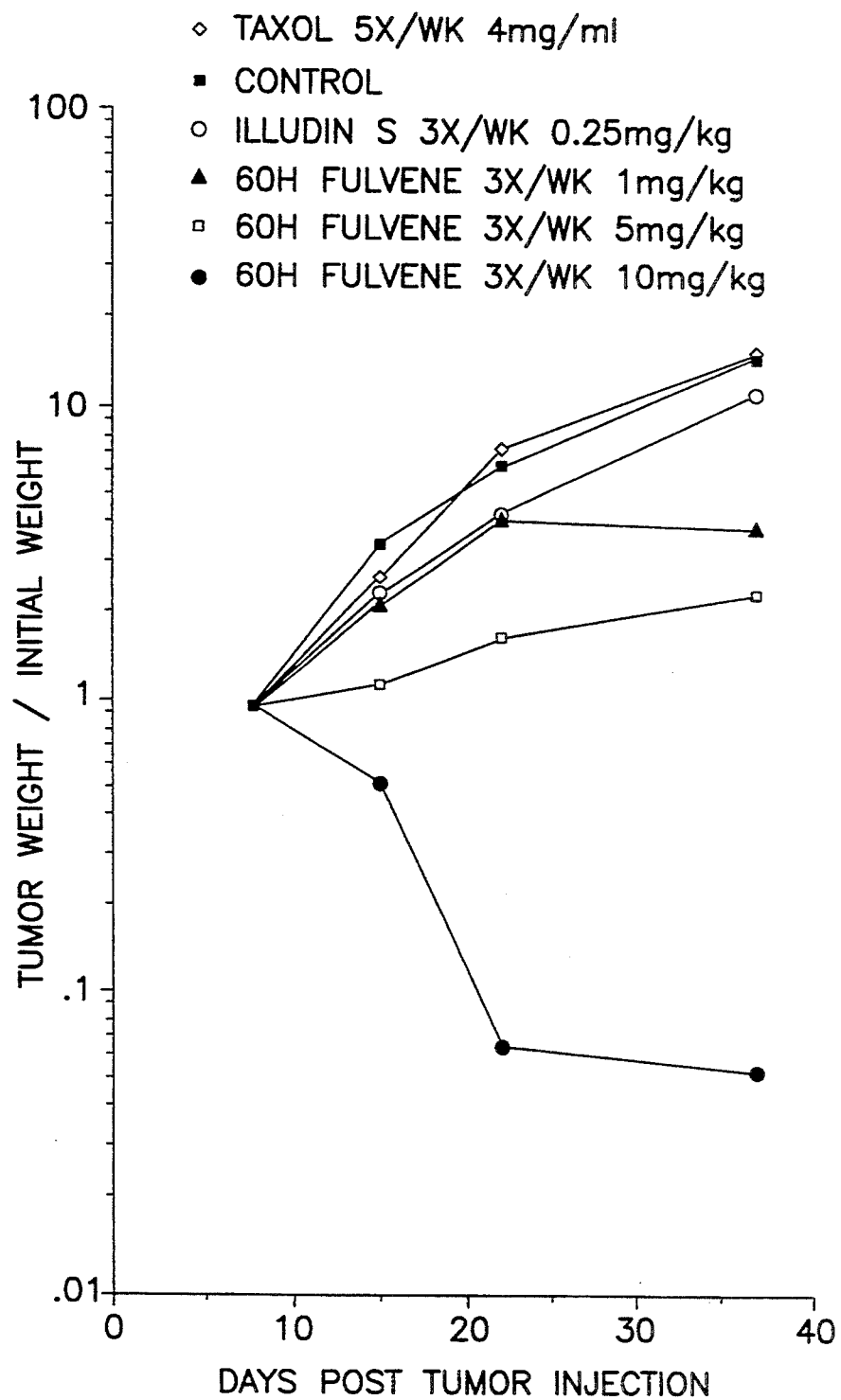
FIG. 11 shows the effect of different doses of 6-hydroxymethylacylfulvene on human lung adenocarcinoma MV522.

The experiment was repeated with different dosages of the 6-hydroxymethylacylfulvene analog to determine if a dose-response pattern was present. Taxol and low dose Illudin S were again included as pharmaceutical controls (Table 11). A control group receiving only the pharmaceutical solvent (40% DMSO/NS) was again included. Tumor regression was again noted at 10 mg/kg, and inhibition of tumor growth was noted with 1 and 5 mg/kg treatment. The taxol and low dose Illudin S again failed to inhibit tumor growth (FIG. 11). In this second experiment there was again no significant increase in the life span of taxol or Illudin S treated animals as compared controls (40% DMSO/NS treated animals). The 10 mg/kg 6-hydroxymethylacylfulvene and 5 mg/kg 6-hydroxymethylacylfulvene treated animals lived significantly longer than controls (DMSO/NS treated), taxol, or Illudin S treated animals. The probability (or significance) value for 10 mg/kg 6-hydroxymethylacylfulvene treated animals versus the controls, taxol treated, and Illudin S treated animals was less than 0.001 in each case ($p < 0.001$). The probability value for the 5 mg/kg 6-hydroxymethylacylfulvene treated animals versus the controls, taxol treated, and Illudin S treated animals was also less than 0.001 in each case ($p < 0.001$). The 1 mg/kg 6-hydroxymethylacylfulvene treated animals also lived significantly longer than the control group ($p < 0.01$).

TABLE 11

Efficacy of 6-hydroxymethylacylfulvene analog, versus other agents, in the human lung adenocarcinoma MV522 metastatic lung tumor model - Second experiment

| | drug | life span |
|---|---|---|
| controls DMSO/NS | IP 3×/WK | 100 ± 16% |
| | | (100% by definition) |
| taxol | 4.0 mg/kg IP 5×/WK | 120 ± 10% |
| | | (not significant) |
| Illudin S | 0.25 mg/kg IP 3×/WK | 104% ± 20% |
| 6-hydroxymethylacylfulvene | 10 mg/kg IP 3×/WK | 232 ± 20% |
| 6-hydroxymethylacylfulvene | 5 mg/kg IP 3×/WK | 154 ± 13% |
| 6-hydroxymethylacylfulvene | 1 mg/kg IP 3×/WK | 135 ± 10% |

The experiment was repeated for a third time (Table 12). The amount of taxol administered IP was increased to demonstrate maximum dosage, and a subcutaneous dosage was added due to reports that this route may be more efficacious. Adriamycin and mitomycin C were again included. Two of the new acylfulvene derivatives (iodoacylfulvene and the p-hydroxybenzylfulvene) were included in this experiment. The diketone analog was included to demonstrate the marked improvement of the 6-hydroxymethylacylfulvene. The 6-hydroxymethylacylfulvene markedly increased the life span versus controls and all other drug treated animals. The probability (or significance) value for the 6-hydroxymethylacylfulvene versus all the control group, the mitomycin C treated group, the adriamycin treated group, and both of the taxol treated groups was less than 0.0005 ($p<0.0005$). This is an extremely significant effect. It is important to note that based on the longevity of 2 particular animals, there is the possibility they may have been cured. Although the diketone also markedly increased the lifespan versus controls ($p<0,002$) and other drug treated animals, it was not as effective as the 6-hydroxymethylacylfulvene. Note that the lifespan of the high dose taxol treated animals (6 mg/kg IP) not only decreased below that of the 4 mg/kg taxol treated animals in the previous experiment, but it was now less than the life span of untreated or control animals. This indicates that the maximum dose for taxol had been reached and drug toxicity was now killing the animals. The other new analogs, the iodoacylfulvene and the p-hydroxybenzylfulvene are also effective in this model.

TABLE 12

Efficacy of 6-hydroxymethylacylfulvene analog, versus other agents, in the human lung adenocarcinoma MV522 metastatic lung tumor model - Third experiment

| | drug | life span |
|---|---|---|
| controls DMSO/NS IP 3×/WK | | 100 ± 29% |
| taxol | 6.0 mg/kg IP 5×/WK | 93 ± 22% |
| taxol | 20.0 mg/kg IP 5×/WK | 113 ± 22% |
| mitomycin C | 2.4 mg/kg IP 1×/WK | 149 ± 12% |
| adriamycin | 2.6 mg/kg IP 1×/WK | 105 ± 25% |
| diketone 30 mg/kg IP 3×/WK | 163 ± 6% | |
| (listed original application) | | |
| iodoacylfulvene | 20 mg/kg IP 3×/WK | 120 ± 34% |
| p-hydroxybenzylfulvene | 15 mg/kg IP 3×/WK | 125 ± 16% |
| p-hydroxybenzylfulvene | 20 mg/kg IP 3×/WK | 126 ± 22% |
| 6-hydroxymethyl-acylfulvene | 10 mg/kg IP 3×/WK (2 animals alive, ? cured) | >204% |

Although the invention has been described with reference to the presently-preferred embodiment, it should be understood that various modifications can be made without departing from the spirit of the invention. Accordingly, the invention is limited only by the following claims.

We claim:

1. A therapeutic method of inhibiting rumor cell growth in a subject in need of said therapy comprising parenterally administering a therapeutic amount of a compound in a pharmaceutically acceptable carrier, wherein said compound has the structure:

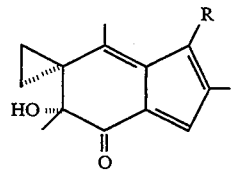

wherein R is selected from the group consisting off

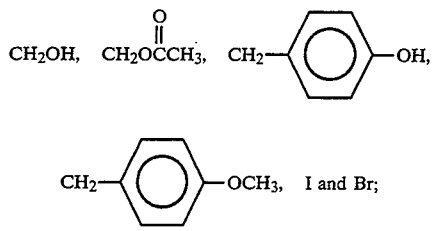

and wherein said rumor cell is sensitive to inhibition by said compound and is selected from the group consisting of a myeloid leukemia cell, a T-cell leukemia cell, a lung carcinoma cell, an ovarian carcinoma cell, and a breast carcinoma cell.

2. The method of claim 1 wherein administering the compound comprises intravenously administering the compound to the subject.

3. The method of claim 2 wherein the therapeutic amount is between 30 to 112,000 μg per kg of body weight.

4. The method of claim 1 wherein administering the compound comprises intraperitoneally administering the compound to the subject.

5. The method of claim 4 wherein the therapeutic amount is between 300 to 112,000 μg per kg of body weight.

6. The method of claim 1 wherein R is CH$_2$OH.

7. The method of claim 1 wherein R is Br.

8. The method of claim 1 wherein R is I.

9. The method of claim 1 wherein R is

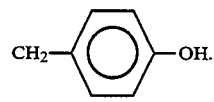

10. The method of claim 1 wherein R is

CH$_2$—⟨benzene⟩—OCH$_3$.

11. The method of claim 1 wherein R

CH$_2$OCCH$_3$ (with =O).

12. A therapeutic composition comprising 30 to 100 mg of the compound of claim 1 and a pharmaceutically acceptable carrier.

* * * * *

UNITED STATES PATENT AND TRADEMARK OFFICE
CERTIFICATE OF CORRECTION

PATENT NO. : 5,439,936

DATED : August 8, 1995

INVENTOR(S) : Kelner et al.

It is certified that error appears in the above-indentified patent and that said Letters Patent is hereby corrected as shown below:

Column 1, Line 64, please delete "these" and insert --there-- therefor.

Column 3, line 28, under DETAILED DESCRIPTION OF THE INVENTION, Structure Three, please delete "$CH_2OCR_1$"

Column 12, Line 28, please delete "92" and insert --8392-- therefor.

Column 19, Line 61, please delete "inhibiting rumor" and insert --inhibiting tumor-- therefor.

Column 20, Line 22, please delete "said rumor" and insert --said tumor-- therefor.

Column 20, Line 10, please delete "consisting off" and insert --consisting of-- therefor.

Signed and Sealed this

Eleventh Day of June, 1996

Attest:

BRUCE LEHMAN

*Attesting Officer*     *Commissioner of Patents and Trademarks*